(12) United States Patent
Berdia

(10) Patent No.: US 10,123,838 B2
(45) Date of Patent: Nov. 13, 2018

(54) DRAPES WITH CIRCUMFERENTIAL AND LONGITUDINAL BREAKAWAYS

(71) Applicant: Sunjay Berdia, Potomac, MD (US)

(72) Inventor: Sunjay Berdia, Potomac, MD (US)

( * ) Notice: Subject to any disclaimer, the term of this patent is extended or adjusted under 35 U.S.C. 154(b) by 400 days.

(21) Appl. No.: 14/098,203

(22) Filed: Dec. 5, 2013

(65) Prior Publication Data

US 2014/0150805 A1 Jun. 5, 2014

Related U.S. Application Data

(60) Provisional application No. 61/733,546, filed on Dec. 5, 2012.

(51) Int. Cl.
| | |
|---|---|
| *A61B 19/08* | (2006.01) |
| *A61B 19/12* | (2006.01) |
| *A61B 46/00* | (2016.01) |
| *A61B 46/27* | (2016.01) |

(52) U.S. Cl.
CPC ............ *A61B 19/088* (2013.01); *A61B 46/00* (2016.02); *A61B 46/27* (2016.02); *A61B 46/40* (2016.02)

(58) Field of Classification Search
CPC ..... A61B 19/08–19/12; Y10T 24/1636; Y10T 24/3776; Y10T 24/3768
USPC ...................... 24/391, 394, 397, 714.6, 714.9
See application file for complete search history.

(56) References Cited

U.S. PATENT DOCUMENTS

| | | | | |
|---|---|---|---|---|
| 3,153,413 A * | 10/1964 | Gottfried | .................. | 602/60 |
| 3,799,161 A * | 3/1974 | Collins | ................... | A61B 46/00 128/854 |
| 3,826,253 A * | 7/1974 | Larsh | ..................... | A61B 46/00 128/854 |
| 3,862,632 A * | 1/1975 | Hinsch | ................... | A61B 46/30 128/849 |
| 3,882,859 A * | 5/1975 | Ericson | .................. | A61B 46/00 128/854 |
| 4,316,456 A * | 2/1982 | Stoneback | ............. | A61B 46/00 128/852 |
| 5,178,162 A * | 1/1993 | Bose | ....................... | A61B 46/27 128/849 |
| 5,538,012 A * | 7/1996 | Wiedner | ................. | A61B 46/00 128/849 |
| 5,682,654 A * | 11/1997 | Crowley et al. | ............. | 24/714.9 |
| 5,778,890 A * | 7/1998 | Lofgren | ................. | A61B 46/00 128/849 |
| 5,800,483 A * | 9/1998 | Vought | ...................... | A61F 7/00 128/849 |
| 5,860,420 A * | 1/1999 | Wiedner | ................ | A61B 46/00 128/849 |
| 5,991,666 A * | 11/1999 | Vought | ..................... | A61F 7/00 128/849 |
| 7,775,213 B2 * | 8/2010 | Henke-Sarmento | ... | A61B 46/10 128/852 |

(Continued)

Primary Examiner — Kari Rodriquez
(74) *Attorney, Agent, or Firm* — Attentive Law Group, PLLC; Paul Ratcliffe

(57) ABSTRACT

The present invention is a surgical drape that has several circumferential and longitudinal breakaway sections that can be easily removed to facilitate quick customization during surgery. The removable sections are fastened to the drape in a manner that reduces debris, which could cause contamination of the surgery field, as well as limit the potential injury to patients caused by the current use of scissors to customize drapes while in surgery.

9 Claims, 2 Drawing Sheets

(56) References Cited

U.S. PATENT DOCUMENTS

| | | | |
|---|---|---|---|
| 8,196,586 B2* | 6/2012 | Henke-Sarmento | A61B 46/10 128/852 |
| 2009/0255541 A1* | 10/2009 | Kaska | A61B 46/10 128/853 |
| 2010/0031966 A1* | 2/2010 | Allen | A61B 46/00 128/851 |
| 2011/0146694 A1* | 6/2011 | Fischer et al. | 128/856 |
| 2011/0284012 A1* | 11/2011 | McCollough | A61B 46/23 128/852 |
| 2011/0297164 A1* | 12/2011 | Strauch | A61B 19/088 128/849 |

\* cited by examiner

DRAPES WITH CIRCUMFERENTIAL AND LONGITUDINAL BREAKAWAYS

RELATED APPLICATION

This application claims priority to U.S. Provisional Patent Application 61/733,546 filed on Dec. 5, 2012, entitled "Drapes with Circumferential and Longitudinal Breakaways", the entirety of which is incorporated herein.

BACKGROUND OF THE INVENTION

1. Field of the Invention

The present invention relates generally to a surgical drape that has several circumferential and longitudinal breakaway sections that can be easily removed to facilitate quick removal of one or more drape sections to enable customization of the drape prior to or during surgery while reducing or minimizing debris.

2. Description of the Related Art

Presently, surgical drapes come in various shapes and sizes designed to fit the contours of the body. For example, there are rectangular drapes, U-shaped drapes, and tube stockinettes. These drapes may also include various cut-outs or windows to best fit the drape to the body and/or frame a surgical site. When draping, it is common for drapes to be layered over and around the surgical site thus creating a frame, window or fenestration. However, during the draping process, scrubbed team members may be required to further customize the drapes in order to make them the right size for the surgical site. In order to do so, this requires that the drape be cut with scissors or modified in some other manner. However, the use of scissors to customize surgical drapes and stockinettes may contaminate the surgical field as well as cause potential injury to the patient. Therefore, what is needed is a surgical drape or stockinette that includes circumferential and longitudinal breakaways allowing for customization of the opening without contaminating the sterilized environment while limiting potential patient injury.

SUMMARY OF THE INVENTION

This summary is provided to introduce concepts in a simplified form that are further described in the detailed description of the invention. This summary is not intended to identify key or essential inventive concepts of the claimed subject matter, nor is it intended for determining the scope of the claimed subject matter.

The present invention provides a sterile surgical drape or stockinette that has several circumferential and longitudinal breakaway sections that enable one or more drape sections to be removed and discarded to facilitate quick customization prior to or during surgery. The removable sections or panels are fastened or connected to each other to form one drape or stockinette. The drape or stockinette is ideally suited for an extremity such as an arm or leg. Sections or panels can be removed from the drape in a manner that minimizes debris as such debris can contaminate the surgical field. In addition to minimizing the debris, the detachable sections of the drape and the detachment mechanism or design minimizes or limits the potential injury to patients compared with the current standard drapes used in surgery today where scissors are used. Scissors are used to cut current drapes to the appropriate customized length for surgery as well as to remove any sections to provide access to a particular area on the patient.

One embodiment of the present invention is a medical drape comprising: two or more drape panels wherein each panel is comprised of a drape material and has at least one attachment edge for connecting to other panels; at least one fastening device for connecting an attachment edge of a first drape panel to the attachment edge of a second drape panel; wherein the fastening device is comprised of at least two mating elements each mating element running the approximate length of the first attachment edge and the second attachment edge which mate together to connect the one or more drape panels; and a connecting piece which interconnects the mating elements, wherein upon removal of the connecting piece the mating elements can be separated and the drape panels separated. In another embodiment, the medical drape comprises a stockinette.

In one embodiment, this medical drape has at least two mating elements that are coils and the connecting piece is a linear string intertwined between the mating coils. These coils may be made of plastic. Additionally, in one embodiment, the coils are connected to the edge of the panel by stitching.

In another embodiment, the medical drape's mating elements are a line of mating teeth and the connecting piece is a slider bow which mates the teeth to connect the panels or when removed separates the teeth. These teeth could be plastic. Also, these teeth could be placed along a longitudinal tape section which is attached to the edge of the panel.

These and other objects, features, and/or advantages may accrue from various aspects of embodiments of the present invention, as described in more detail below.

BRIEF DESCRIPTION OF THE DRAWINGS

The foregoing summary, as well as the following detailed description of the invention, is better understood when read in conjunction with the appended drawing. For the purpose of illustrating the invention, exemplary constructions of the invention are shown in the drawings. However, the invention is not limited to the specific methods and instrumentalities disclosed herein.

DETAILED DESCRIPTION OF EXEMPLARY EMBODIMENTS

Particular embodiments of the present invention will now be described in greater detail with reference to the figures.

Figure 1:
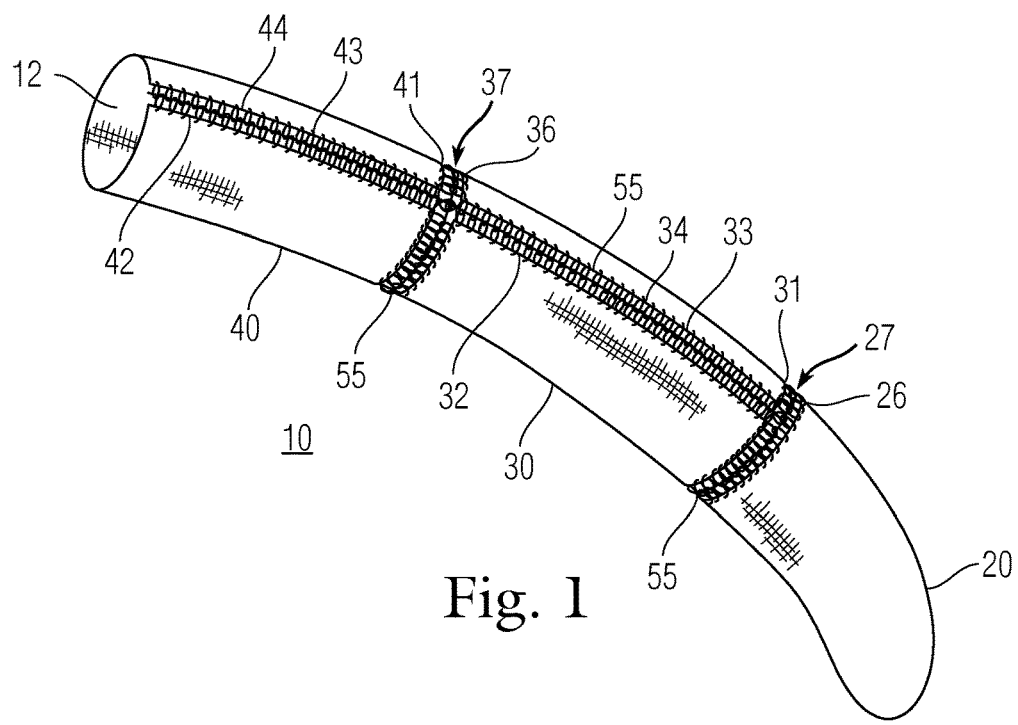
FIG. 1 illustrates a first embodiment of the present invention.

In accordance with FIG. 1, a first embodiment of the present invention provides a surgical drape or stockinette 10 with several sections 20, 30, 40 that can be easily removed prior to or during surgery to quickly gain access to the surgery field. The drape 10 may be made of sterile two-ply material such as cotton, plastic, or paper material, and may include, for example, carbon fiber, ABS plastic, polyurethane, rubber, latex, synthetic rubber, or polymer elements. The drapes 10 material may include a liquid resistant layer and a liquid absorbent layer to keep the patient and the surgical area dry and sterile. In the preferred embodiment, the drape 10 is made from an impervious material. The drape 10 could be shaped as a stockinette or tube (see FIG. 1) for fitting over extremities, or as a rectangle sheet (see FIG. 3) which lays over the patient's entire body or a part of the body. In the preferred embodiment, the drape 10 would be sterile so it could be used in the operating room and as part of the draping process of an arm or leg. In addition, the drape 10 would be disposable to limit the risk of contamination. The color of the drape may vary, though ideally it would be blue and white as common in the medical field.

Figure 3:
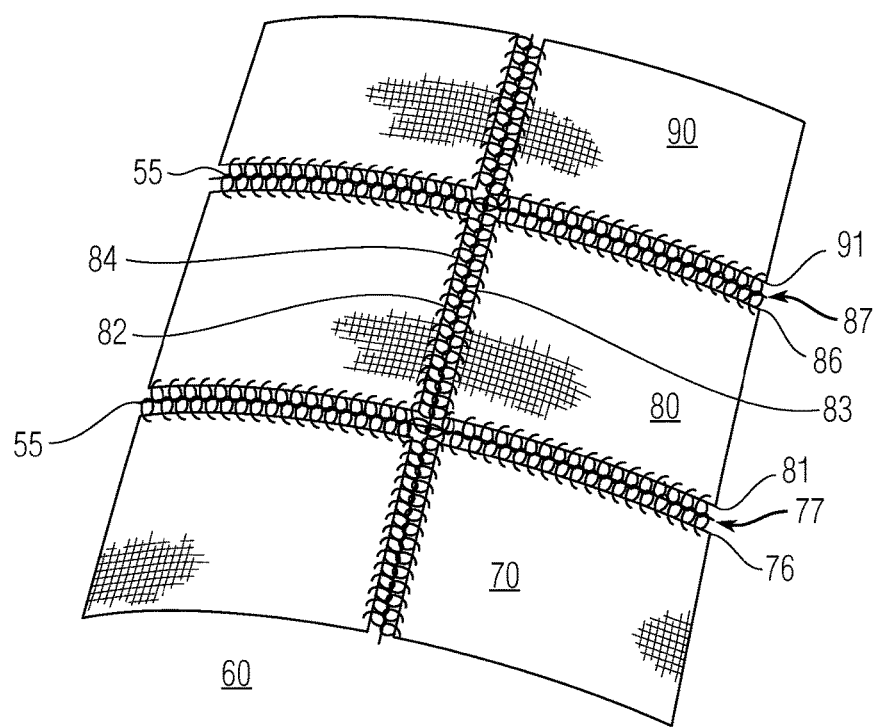
FIG. 3 illustrates a second embodiment of the present invention.

In one exemplary embodiment, FIG. 3, the drape 60 would have a rectangular shape with standard and non-standard dimensions including up to 250×250 cm which could cover the patient's entire body. In other embodiments, FIG. 1, the drape 10 would be considered an extremity stockinette and may cover only a portion of the patient's body such as his arm or leg. The stockinette 10 would come in a set of sizes such as extra small, small, medium, large, and extra large so as to allow it to fit different patient extremity sizes. The set stockinette size would not only determine the circumference variance of the tube but also the overall length of the stockinette 10.

In the operating room, this sterile stockinette or drape 10 is pulled or rolled over that patient's extremity through opening 12 after the extremity's skin is sterilized. Once the stockinette or drape 10 is fitted on the extremity, it is brought through a separate drape (not shown) with a hole that is then fully opened to cover the rest of the body and operating room's table, thus creating a complete sterile field. However, at this point the entire body and the extremity are covered. Therefore, in order to perform a surgical procedure on the extremity, portions of the drape must be removed to provide a frame or window to the area on the extremity which needs the procedure.

Therefore, the stockinette or drape 10 has several removable sections 20, 30, 40 throughout the drape 10 that allows for quick customization of the drape 10 so it can be used in a variety of surgeries. For example, the drape 10 configured or sized for application over an arm can have sections 20, 30, 40 removed to provide access to the wrist, hand, forearm, elbow, or upper arm for the procedure or surgery. The drape 10 might also be sized fit over a patient's leg so it can be used to perform surgery on a patient's foot, ankle, calf, knee, or thigh. These sections are again removed by disconnecting the panel 20, 30, 40 from the drape 10 and exposing just the area of the arm or leg that is undergoing surgery.

In one embodiment, the sections 20, 30, 40 can be removed by utilizing a circumferential breakaway 27, 37 to shorten the length of the drape 10 on an extremity. This means there are several circumferential breakaways 27, 37 which may be equidistant apart running along the width of the drape that allows for quick and easy customization. This prevents the potential contamination of a sterile environment that may occur when the drape is "rolled up" or cut to acquire the appropriate length.

In another embodiment, there are several sections 20, 30, 40 on the drape 10 that utilize a combination of circumferential breakaways 27, 37 and longitudinal breakaways 34, 44. These allow the middle section 30 to be removed in a manner that exposes only a specific portion of the extremity. An example of this for an upper extremity would be to allow just the elbow to be exposed while leaving the arm and forearm covered.

The lower circumferential breakaway point or edge 31, 41 of a section 30 and section 40 is fastened to the upper circumferential breakaway point 26, 36 of an adjacent section 20 and 30 by a fastener 55. The left longitudinal breakaway point or edge 32 and 42 of the left middle and upper section is secured to the right longitudinal breakaway point or edge 33, 43 by a fastener 55. These fasteners 55 allow for quick removal with limited debris. The fasteners 55 may be zip strips, cohesive or adhesive material, pins, buttons, clips, ties, snaps, zippers, hook and loop devices (i.e. a Velcro like material), perforated tear strips, magnetic strips, or lace and interconnected coils.

Figure 2A:
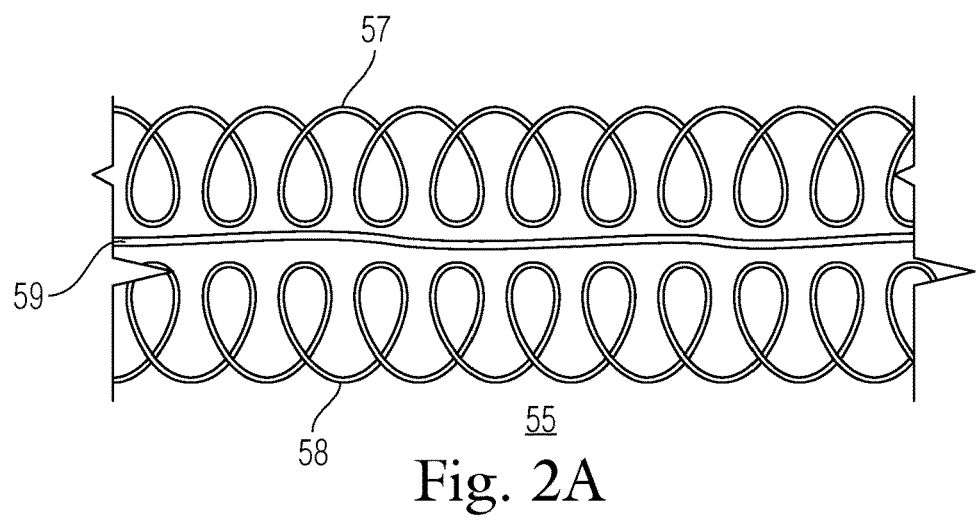
FIG. 2A illustrates a profile view of one embodiment of the fastening mechanism of the present invention in an unfastened state.
Figure 2B:
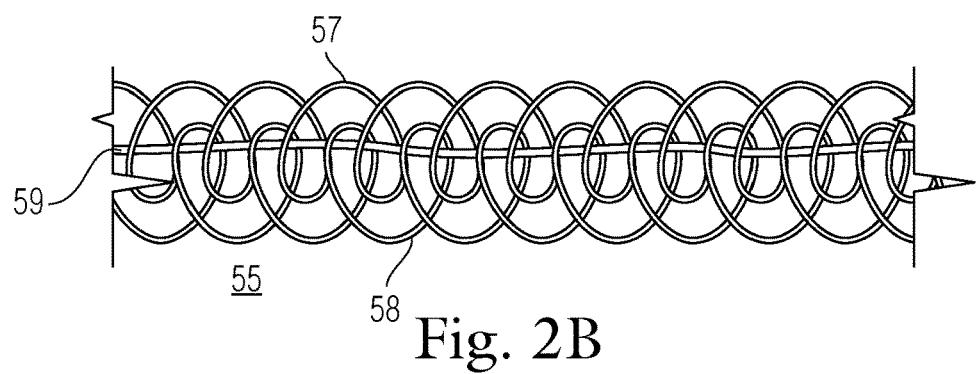
FIG. 2B illustrates a profile view of one embodiment of the fastening mechanism of the present invention in a fastened state.

FIG. 2 shows one embodiment of a fastener 55 where the drape sections 20, 30, 40 are attached by a fastener 55 that incorporates two coils 57, 58 and a single piece of lace or string 59. These coils 57, 58 may be made out of a flexible material such as plastic, metal, or cotton. The lace 59 is also made out of a flexible material which may be plastic or cotton or other. The two coils 57, 58 run parallel to each other and can be pushed together causing the coils to interconnect creating one unobstructed opening. The lace 59 is threaded through the opening to keep the interconnected coils in place preventing them from separating. Once the lace 59 is cut and taken out, the coils 57, 58 easily separate allowing for the breakaway section to be removed.

By way of example, if a doctor is preparing a patient for an elbow surgery, the doctor would roll the drape 10 up the patient's arm which had been inserted into opening 12. The doctor would then cut the lace 59 along circumferential opening 27 and 37 and remove the lace 59 from the coils 57, 58. Once detached panels 20, 30, and 40 would be separated. However, the doctor still needs to remove panel 30 from the patient's arm. The doctor would then cut and remove lace 59 along longitudinal joint 33. After separating joint 33 the panel 30 could be easily removed from the patient's arm.

The fastener 55 is attached to the edges of the drape panels or sections 20, 30, 40. In one embodiment, the fastener 55 is attached to the edges of panels 20, 30, 40 via an adhesive, such as glue. For example, the fastener 55 may be glued to one side of the drape panel 20, 30, 40. Optionally, the fastener 55 is glued to the back side of the drape panel 20, 30, 40, or attached to the edge of the drape panel 20, 30, 40. In another embodiment, the fastener 55 is stitched into the panels 20, 30, 40.

In a further embodiment, the fastener 55 is integrated into the design of the drape edge manufacturing. For example, the drape edge may be plastic formed via a think panel mold. The mold for the drape 10 would automatically have fastening elements designed into the mold such that the fastening edges would be produced with the mating elements already integrated. For our example, the plastic teeth element of a zipper design or plastic coil elements of the coil and lace design could be integrated into the drape mold. Further, the manufacturing process of the drape could incorporate the teeth or coil design as a separate component which the plastic sheeting of the drape panel is formed around and then allowed to cure or cool to interconnect the teeth or coil 57, 58. The fastener 55 could also be attached to the drape panels 20, 30, 40 by utilizing a 3d printer that prints the fastener 55 onto the edges of the drape panels 20, 30, 40 in a manner that securely attaches it to the panels and the panels or mating elements to each other.

The coil fastener 55 depicted in FIG. 2 could also be wound through the drape panels 20, 30, 40. For example, the coil 57, 58, itself, would be "stitched" into the drape fabric by winding it repeatedly through the panel until it has been wound through the entire length of the drape. This could be done during the curing of the drape plastic edges or after curing.

FIG. 3 displays a second embodiment of the drape 60 in which the drape is rectangular shape and lays over the patient's entire body. The sections 70, 80, 90 are attached together by latitudinal breakaways 77, 87 and longitudinal breakaways 84. The upper latitudinal breakaway point or edge 81, 91 of a section 70, 80, 90 is secured to the lower latitudinal breakaway point or edge 76, 86 of a section by a fastener 55. The left longitudinal breakaway point or edge 82 of the left section is secured to the right longitudinal breakaway point 83 of a section by a fastener 55.

In use, the drape 60 is applied or draped over a patient and sections of the drape may be removed. For example, if the drape 60 was draped over a patient that needed hip surgery, the surgical team could remove panel or section 80 by separating fastener 55 around panel 80. In the preferred embodiment, fastener 55 would use the lace and coil design previously described.

The drapes and stockinettes 10, 60 described herein are representative examples. The drapes 10, 60 could have more panels or sections 20, 30, 40, 70, 80, 90 in the design to enable doctors to create smaller openings or windows. Further, some drapes 10, could be specifically designed for known procedures, such as having a full drape 10 with only one center panel which can be removed such as would be useful for a procedure on the chest or stomach.

The examples provided herein are merely for the purpose of explanation and are in no way to be construed as limiting of the present method and product disclosed herein. While the invention has been described with reference to various embodiments, it is understood that the words which have been used herein are words of description and illustration, rather than words of limitation. Further, although the invention has been described herein with reference to particular means, materials, and embodiments, the invention is not intended to be limited to the particulars disclosed herein; rather, the invention expands to all functionally equivalent structures, methods and uses, such as are within the scope of the appended claims. Those skilled in the art, having the benefit of the teachings of this specification, may affect numerous modifications thereto and changes may be made without departing from the scope and spirit of the invention.

It will be recognized by those skilled in the art that changes or modifications may be made to the above described embodiment without departing from the broad inventive concepts of the invention. It is understood therefore that the invention is not limited to the particular embodiment which is described, but is intended to cover all modifications and changes within the scope and spirit of the invention.

What is claimed is:

1. A medical drape comprising:
   a first drape panel and a second drape panel wherein the first and second drape panel is comprised of a drape material;
   the first drape panel having a first attachment edge for connecting to a second attachment edge of the second drape panel;
   a fastening device for connecting the first attachment edge of the first drape panel to the second attachment edge of the second drape panel;
   wherein the fastening device is comprised of at least two mating elements with a first mating element connected to the first attachment edge and a second mating element connected to the second attachment edge;
   the first mating element constituted by a first joined sequence of first mating element portions, each first mating element portion defined by a plurality of first coils having a first coil space between each coil and a transverse change in direction relative to the second mating element;
   the second mating element constituted by a second joined sequence of second mating element portions, each second mating element portion defined by a plurality of second coils with a second coil space between each coil and a transverse change in direction relative to the first mating element;
   the first mating element and the second mating element configured to mate together constituted by the first mating element in a dovetail relationship with the second mating element, such dovetail relationship including:
   (a) each coil of the plurality of first coils from the first mating element portions, in the first joined sequence, extending within the space between each coil of the plurality of second coils of the second mating element portions, and
   (b) each coil of the plurality of second coils from the second mating element portions, in the second joined sequence, extending within the space between each coil of the plurality of first coils of the first mating element portions; and
   a connecting piece which interconnects the first mating element and the second mating element together, wherein upon removal of the connecting piece the first and second mating elements can be separated allowing the first and second drape panels to be separated.

2. The medical drape of claim 1, the connecting piece is a linear string running lengthwise between the plurality of first coils and the plurality of second coils.

3. The medical drape of claim 2, wherein the coils are plastic.

4. The medical drape of claim 3, wherein the first mating element is connected to the first attachment edge of the panel by stitching.

5. A medical drape comprising: a first drape panel; wherein the first drape panel has a first edge and a second edge and a first mating element is attached along the first edge and a second mating element is attached along the second edge;
   the first mating element having a plurality of first coils and the second mating element having a plurality of second coils, wherein the mating elements are configured to mate together with the plurality of first coils interleaved with the plurality of second coils to connect the first edge to the second edge; and a linear string running through the interleaved plurality of first and second coils;
   wherein upon mating the first mating element and second mating element, and connecting the first and second elements with the connecting piece, the drape panel forms a stockinette.

6. A medical drape comprising:
   a first panel is comprised of a drape material having a first attachment edge for connecting to a second attachment edge on a second panel;
   a fastening device for connecting the first attachment edge of the first panel to the second attachment edge of the second panel;
   wherein the fastening device is comprised of a first mating element having a plurality of first coils with a plurality of first spaces between each first coil and a second mating element having a plurality of second coils with a plurality of second spaces between each second coil;

the first mating element and the second mating element are configured to mate together with the plurality of first coils interleaved with the plurality of second coils, wherein the plurality of first coils are inserted within the plurality of second spaces between each second coil and the plurality of second coils are inserted within the plurality of first spaces between each first coil, to connect the first panel to the second panel; and a linear string runs through the interleaved plurality of first and second coils, wherein upon removal of the linear string the first mating element and second mating element can be separated and the drape panels separated.

7. The medical drape of claim 6, wherein the first mating element and second mating element are plastic.

8. The medical drape of claim 7, wherein the first mating element is connected to the first attachment edge of the panel by stitching.

9. A method for separating a first medical drape panel from a second medical drape panel comprising:

removing a string which runs through a channel of an coil assembly;

the interleaved coil assembly comprising a first mating element with a plurality of first coils with a plurality of first spaces between each first coil, and a second mating element with a plurality of second coils with a plurality of second spaces between each second coil, wherein the plurality of first coils are placed-within the plurality of second spaces and the plurality of second coils are placed within the plurality of first spaces to form the channel;

wherein the first mating element is attached to the first medical drape and the second mating element is attached to the second medical drape;

separating the first medical drape panel from the second medical drape panel by separating the first mating element from the second mating element by removing the plurality of first coils from the plurality of second spaces and the plurality of second coils from the plurality of first spaces.

* * * * *